(12) United States Patent
Meagher

(10) Patent No.: US 10,736,627 B2
(45) Date of Patent: Aug. 11, 2020

(54) ANASTOMOTIC STAPLE WITH CAPILLARY WHICH EXPELS A BONDING AGENT UPON DEFORMATION

(71) Applicant: Covidien LP, Mansfield, MA (US)

(72) Inventor: Edward Meagher, Greenlawn, NY (US)

(73) Assignee: COVIDIEN LP, Mansfield, MA (US)

( * ) Notice: Subject to any disclaimer, the term of this patent is extended or adjusted under 35 U.S.C. 154(b) by 132 days.

(21) Appl. No.: 16/144,359

(22) Filed: Sep. 27, 2018

(65) Prior Publication Data

US 2019/0021731 A1 Jan. 24, 2019

Related U.S. Application Data

(63) Continuation of application No. 15/070,587, filed on Mar. 15, 2016, now Pat. No. 10,092,289, which is a continuation of application No. 12/480,235, filed on Jun. 8, 2009, now Pat. No. 9,301,762, which is a continuation of application No. 10/556,125, filed as application No. PCT/US03/14691 on May 9, 2003, now Pat. No. 8,636,191.

(51) Int. Cl.
| | | |
|---|---|---|
| *A61B 17/068* | (2006.01) | |
| *A61B 17/064* | (2006.01) | |
| *A61B 17/115* | (2006.01) | |
| *A61B 17/00* | (2006.01) | |
| *A61B 17/11* | (2006.01) | |

(52) U.S. Cl.
CPC ........ *A61B 17/0644* (2013.01); *A61B 17/115* (2013.01); *A61B 17/00491* (2013.01); *A61B 17/068* (2013.01); *A61B 17/1114* (2013.01); *A61B 2017/00893* (2013.01); *A61B 2017/0641* (2013.01); *A61B 2017/1107* (2013.01); *A61B 2017/1135* (2013.01)

(58) Field of Classification Search
CPC .......... A61B 17/00491; A61B 17/0644; A61B 17/115
USPC ............................... 606/151, 154; 227/176.1
See application file for complete search history.

(56) References Cited

U.S. PATENT DOCUMENTS

| | | | |
|---|---|---|---|
| 2,671,444 | A | 3/1954 | Pease, Jr. |
| 2,728,116 | A | 12/1955 | Rosenman |
| 3,108,357 | A | 10/1963 | Liebig |

(Continued)

FOREIGN PATENT DOCUMENTS

| | | | |
|---|---|---|---|
| EP | 0537570 | A2 | 4/1993 |
| EP | 0647431 | A2 | 4/1995 |

(Continued)

OTHER PUBLICATIONS

International Search Report from PCT/US03/14691.

(Continued)

*Primary Examiner* — Gloria R Weeks

(74) *Attorney, Agent, or Firm* — Carter, DeLuca & Farrell LLP

(57) ABSTRACT

A surgical fastener for use with an anastomosis of two tissues includes a base leg and an upright leg. The base leg is selectively deformable and includes a traumatic tip for piecing tissue. The surgical fastener also includes at least one capillary disposed on the base leg which has a reservoir defined therein for retaining a liquid, e.g., bioadhesive, bonding agent, medicament, etc. Each of the capillaries is ruptureable upon deformation of the surgical fastener to dispense the liquid to the anastomosis site.

20 Claims, 12 Drawing Sheets

(56) References Cited

U.S. PATENT DOCUMENTS

| | | | |
|---|---|---|---|
| 3,209,754 A | 10/1965 | Brown | |
| 4,275,813 A | 6/1981 | Noiles | |
| 4,535,772 A | 8/1985 | Sheehan | |
| 4,548,202 A | 10/1985 | Duncan | |
| 4,655,222 A | 4/1987 | Florez et al. | |
| 4,719,917 A | 1/1988 | Barrows et al. | |
| 5,156,623 A | 10/1992 | Hakamatsuka et al. | |
| 5,203,864 A | 4/1993 | Phillips | |
| 5,222,975 A | 6/1993 | Crainich | |
| 5,263,629 A | 11/1993 | Trumbull et al. | |
| 5,282,829 A | 2/1994 | Hermes | |
| 5,324,307 A | 6/1994 | Jarrett et al. | |
| 5,342,395 A | 8/1994 | Jarrett et al. | |
| 5,366,479 A | 11/1994 | McGarry et al. | |
| 5,392,979 A | 2/1995 | Green et al. | |
| 5,431,323 A | 7/1995 | Smith et al. | |
| 5,465,896 A | 11/1995 | Allen et al. | |
| 5,497,933 A | 3/1996 | DeFonzo et al. | |
| 5,505,736 A | 4/1996 | Reimels et al. | |
| 5,607,095 A | 3/1997 | Smith et al. | |
| 5,620,289 A | 4/1997 | Curry | |
| 5,630,540 A | 5/1997 | Blewett | |
| 5,717,030 A | 2/1998 | Dunn et al. | |
| 5,738,474 A | 4/1998 | Blewett | |
| 5,759,171 A | 6/1998 | Coelho et al. | |
| 5,816,471 A | 10/1998 | Plyley et al. | |
| 5,941,890 A | 8/1999 | Voegele et al. | |
| 5,980,548 A | 11/1999 | Evans et al. | |
| 6,015,417 A | 1/2000 | Reynolds, Jr. | |
| 6,025,019 A | 2/2000 | Duffy | |
| 6,045,560 A | 4/2000 | McKean et al. | |
| 6,090,131 A | 7/2000 | Daley | |
| 6,187,019 B1 | 2/2001 | Stefanchik et al. | |
| 6,248,117 B1 | 6/2001 | Blatter | |
| 6,325,805 B1 | 12/2001 | Ogilvie et al. | |
| 6,330,965 B1 | 12/2001 | Milliman et al. | |
| 6,408,489 B1 | 6/2002 | Cluggish | |
| 6,629,988 B2 | 10/2003 | Weadock | |
| 6,689,153 B1 | 2/2004 | Skiba | |
| 6,767,356 B2 | 7/2004 | Kanner et al. | |
| 6,769,594 B2 | 8/2004 | Orban, III | |
| 6,817,508 B1 | 11/2004 | Racenet et al. | |
| 6,869,436 B2 | 3/2005 | Wendlandt | |
| 7,147,138 B2 | 12/2006 | Shelton, IV | |
| 7,398,907 B2 | 7/2008 | Racenet et al. | |
| 7,464,846 B2 | 12/2008 | Shelton, IV et al. | |
| 7,780,684 B2 | 8/2010 | Wulc et al. | |
| 7,780,685 B2 | 8/2010 | Hunt | |
| 7,886,951 B2 | 2/2011 | Hessler | |
| 8,875,970 B2 | 11/2014 | Viola | |
| 8,998,059 B2 | 4/2015 | Smith | |
| 9,301,762 B2 | 4/2016 | Meagher | |
| 10,092,289 B2 | 10/2018 | Meagher | |
| 2001/0021858 A1 | 9/2001 | Bolduc et al. | |
| 2002/0065562 A1 | 5/2002 | Storer et al. | |
| 2002/0133181 A1 | 9/2002 | Tong | |
| 2002/0165541 A1 | 11/2002 | Whitman | |
| 2002/0165563 A1 | 11/2002 | Grant et al. | |
| 2003/0181930 A1 | 9/2003 | Milliman et al. | |
| 2003/0183671 A1 | 10/2003 | Mooradian et al. | |
| 2003/0220660 A1 | 11/2003 | Kortenbach et al. | |
| 2004/0028502 A1 | 2/2004 | Cummins | |
| 2004/0044364 A1 | 3/2004 | DeVries et al. | |
| 2004/0092998 A1 | 5/2004 | Sniitin et al. | |
| 2004/0093024 A1 | 5/2004 | Lousararian et al. | |
| 2004/0167572 A1 | 8/2004 | Roth et al. | |
| 2004/0193177 A1 | 9/2004 | Houghton et al. | |
| 2005/0038472 A1 | 2/2005 | Furst | |
| 2005/0113936 A1 | 5/2005 | Brustad et al. | |
| 2005/0136090 A1 | 6/2005 | Falotico et al. | |
| 2005/0145671 A1 | 7/2005 | Viola | |
| 2005/0228341 A1 | 10/2005 | Edgerley | |
| 2006/0200199 A1 | 9/2006 | Bonutti et al. | |
| 2007/0175949 A1 | 8/2007 | Shelton et al. | |
| 2007/0175951 A1 | 8/2007 | Shelton et al. | |
| 2007/0175952 A1 | 8/2007 | Shelton et al. | |
| 2007/0175953 A1 | 8/2007 | Shelton et al. | |
| 2007/0175955 A1 | 8/2007 | Shelton et al. | |
| 2007/0175956 A1 | 8/2007 | Swayze et al. | |
| 2007/0175957 A1 | 8/2007 | Shelton et al. | |
| 2008/0169329 A1 | 7/2008 | Shelton et al. | |
| 2009/0275902 A1 | 11/2009 | Heeps et al. | |
| 2010/0087840 A1 | 4/2010 | Ebersole et al. | |

FOREIGN PATENT DOCUMENTS

| | | |
|---|---|---|
| EP | 0738501 A1 | 10/1996 |
| EP | 1813203 A2 | 8/2007 |
| WO | 9213491 A1 | 8/1992 |
| WO | 97/29694 A1 | 8/1997 |
| WO | 9740760 A1 | 11/1997 |
| WO | 9952489 | 10/1999 |
| WO | 0156533 A2 | 8/2001 |
| WO | 0244278 A1 | 6/2002 |
| WO | 03030743 A2 | 4/2003 |
| WO | 03094746 A1 | 11/2003 |
| WO | 2004/032760 A2 | 4/2004 |
| WO | 2004105621 A1 | 12/2004 |
| WO | 2007030753 A2 | 3/2007 |
| WO | 2007118179 A2 | 10/2007 |

OTHER PUBLICATIONS

European Search Report dated Apr. 17, 2007 for Corresponding Patent Application EP06026840.

International Search Report for corresponding PCT Application—PCT/US06/21524—dated May 28, 2008 (4 Pages).

Detemple, P., "Microtechnology in Modern Health Care", Med Device Technol. 9(9):18-25 (1998).

European Search Report for corresponding EP 08252703.7 dated Oct. 31, 2008 (3 pages).

European Search Report dated Feb. 27, 2009 for Corresponding Patent Application 08253184.9.

European Search Report for corresponding EP 08252703.7 dated Oct. 31, 2008 (7 pages).

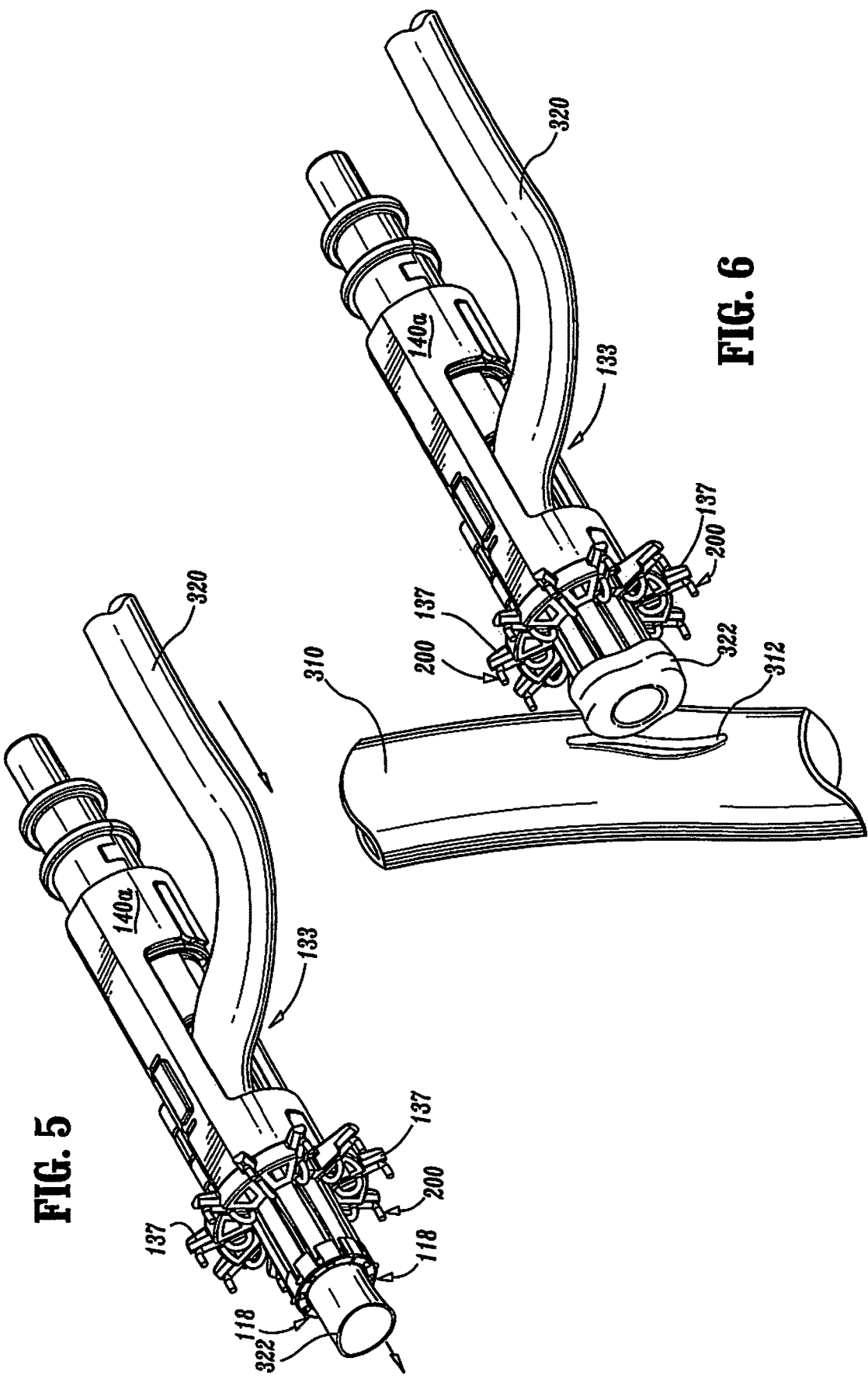

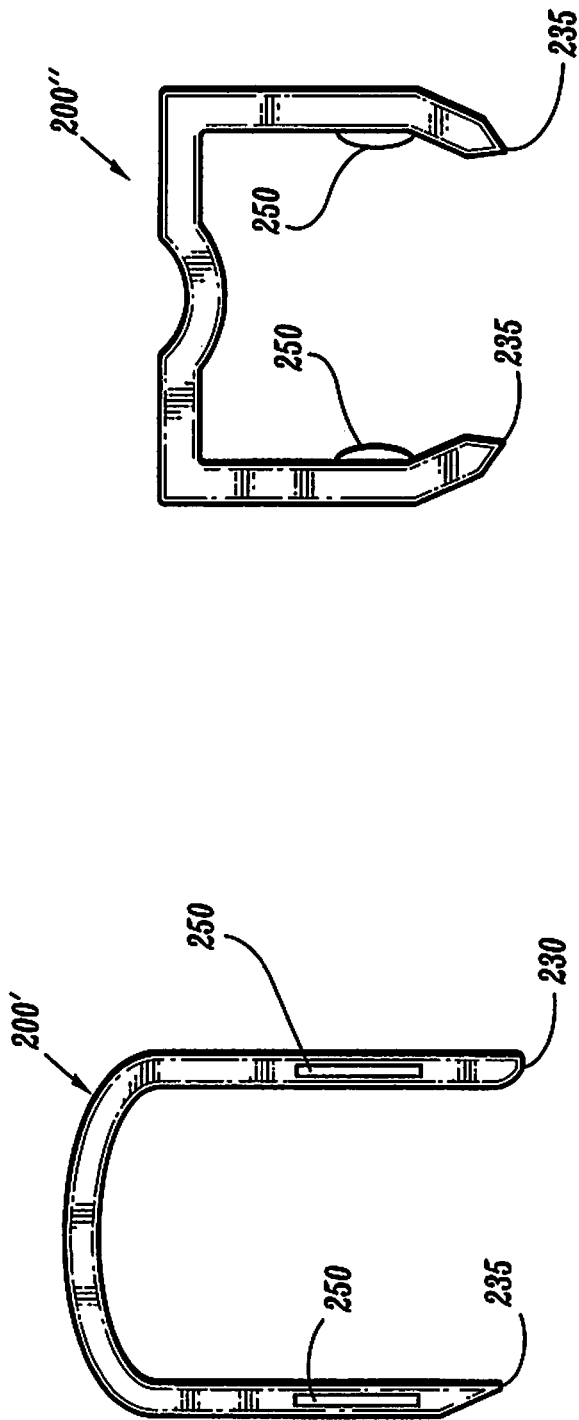

ANASTOMOTIC STAPLE WITH CAPILLARY WHICH EXPELS A BONDING AGENT UPON DEFORMATION

CROSS-REFERENCE TO RELATED APPLICATIONS

The present application is a continuation of U.S. patent application Ser. No. 15/070,587, filed Mar. 15, 2016, which is a continuation of U.S. patent application Ser. No. 12/480,235, filed Jun. 8, 2009, now U.S. Pat. No. 9,301,762, which is a continuation of U.S. patent application Ser. No. 10/556,125, filed on Nov. 9, 2005, now U.S. Pat. No. 8,636,191, which claims the benefit of and priority to PCT Application No. PCT/US2003/14691, filed on May 9, 2003. The entire contents of each the above application are hereby incorporated by reference.

BACKGROUND

1. Technical Field

The present disclosure relates to a surgical staple used for performing an anastomosis of tubular body structures, and more particularly to a surgical staple which includes a capillary disposed thereon which is designed to expel a bonding agent or other medicament upon deformation of the staple.

2. Background of Related Art

Anastomosis is a surgical procedure for joining two tissues, e.g., vessels and tubular organs, for fluid communication therebetween. Generally, anastomosis procedures can be categorized into two main types, coronary artery bypass graft (CABG) procedures and gastrointestinal surgical procedures. A CABG procedure restores blood flow to damaged or ischemic heart muscle whose blood supply has been compromised by occlusion or stenosis of one or more of the coronary arteries. Gastrointestinal anastomosis procedures such as a low anterior resection of the colon are designed to alleviate colon cancer, diverticular disease, gastrointestinal bleeding, inflammatory bowel disease, intestinal polyps and large bowel obstruction.

One method for performing CABG surgery involves harvesting a saphenous vein (or other venous or arterial vessel from elsewhere in the body) and connecting the saphenous vein as a bypass graft from a viable artery, such as the aorta, to the coronary artery downstream of the blockage or narrowing. Such procedures typically require that the heartbeat be arrested while maintaining circulation throughout the rest of the body. Cardioplegic fluid, such as potassium chloride (KCl) is delivered to the blood vessels of the heart to paralyze the myocardium. Cardioplegic fluid is infused into the myocardium through the coronary arteries by a catheter inserted into the ascending aorta. Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is a complicated procedure requiring that the desired vessels be properly located and accessed. The progression of the guide wires and catheters must be closely monitored to determine proper placement. Furthermore, the introduction of catheters form punctures in the blood vessels that must be subsequently closed, and there is an increased risk of trauma to the interior walls of the vessels in which the catheters must pass.

Alternatively, the CABG procedure may be performed while the heart is permitted to beat. Such a procedure is now commonly referred to as minimally invasive direct coronary artery bypass (MIDCAB) when performed through a thoracotomy (when performed through a stemotomy, the procedure is commonly called open coronary artery bypass (OP-CAB). A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform a CABG procedure, the harvested vessel segment, such as the saphenous vein, is grafted to the coronary artery by end-to-side anastomosis. Typically, sutures are used to graft the vessel segments. However, conventional suturing is complicated by the use of minimally invasive procedures, such as the window approach, e.g., limited access and reduced visibility to the surgical site may impede the surgeon's ability to manually apply sutures to a graft. Additionally, it is difficult and time consuming to manually suture if the CABG procedure is being performed while the heart is beating as the suturing must be synchronized with the heart beat.

In order to reduce the difficulty of creating the vascular anastomoses during either open or closed-chest CABG surgery, it would be desirable to provide a rapid means for making a reliable end-to-side or end-to-side anastomosis between a bypass graft or artery and the aorta or the other vessels of the heart. A first approach to expediting and improving anastomosis procedures has been through stapling technology. Stapling technology has been successfully employed in many different areas of surgery for making tissue attachments faster and more reliably. The greatest progress in stapling technology has been in the area of gastrointestinal surgery as described below.

Anastomotic staplers are used commonly for end-to-end anastomosis, side-to-side or end-to-side anastomosis for various coronary artery bypass procedures and gastrointestinal procedures. Surgical stapling devices for applying an array of staples or fasteners to tissue are well known in the art. For example, surgical stapling devices for applying an annular array of staples, as well as devices for completing a surgical anastomosis through the provision of anastomosis rings, are known in gastric and esophageal surgery, e.g., in classic or modified gastric reconstruction typically formed in an end-to-end, end-to-side, or side-to-side manner. Several examples of instruments are shown and described in commonly-owned U.S. application Ser. No. 10/388,969 filed on Mar. 13, 2003 entitled "ANASTOMOSIS INSTRUMENT AND METHOD FOR PERFORMING SAME", commonly-owned U.S. application Ser. No. 10/399,558, filed on Apr. 15, 2003 entitled "ANASTOMOSIS INSTRUMENT AND METHOD FOR PERFORMING SAME", commonly-owned U.S. application Ser. No. 10/191,599 filed on Jul. 8, 2002 entitled "ANASTOMOSIS INSTRUMENT AND METHOD" and commonly-owned U.S. application Ser. No. 10/160,460 filed on May 31, 2002 entitled "END-TO-END ANASTOMOSIS INSTRUMENT AND METHOD FOR PERFORMING SAME" the contents of all of which are incorporated by reference herein. These devices generally include a circular array of fasteners such as staples and an anvil member. The staples are deformed against the anvil member to complete the anastomosis.

In use in gastrointestinal surgery, the anvil is positioned within the lumen of an organ such as the stomach, esophagus, or intestine and the tissue is pulled about and around the anvil member and tied off, e.g., by a purse string suture, ring mechanism or the like. The stapler assembly is then positioned within the opposite end of the lumen and the tissue is pulled about and around the stapler assembly over the staple array and also tied off. At this point the tissue is positioned between the anvil and the stapler assembly. The anvil is typically slowly retracted (or advanced) to approximate the two tissue halves prior to deformation of the staples usually by virtue of a wing-nut and worm gear assembly which allows a surgeon to methodically advance the anvil towards the staple array to hold the tissue between the anvil and the stapler assembly. Many prior art devices also provide a visual indicator to signal the surgeon when the anvil has reached a firing position adjacent the stapler assembly. The surgeon then unlocks a safety device deform the staples against the anvil. As the staples are expelled from the stapler assembly, a circular knife typically follows the application of the staples to excise unwanted tissue at the anastomosis site. The instrument is then removed from the lumen of the organ.

Since it is essential that each anastomosis provide a smooth, open flow path for the blood and that the attachment be completely free of leaks, there is often a frequent need for re-suturing of the anastomosis to close any leaks that are detected once the site is tested. Leaks may be attributed to any number of factors one of which is slippage of the tissue along the staple after the anastomosis. Commonly-owned U.S. patent Ser. No. 10/160,460 describes a retaining ring or strap which is designed for use during an anastomosis which is designed to prevent slippage between the two luminal vessels after the anastomosis. The ring maintains a reliable and consistent anastomosis between the two luminal vessels after the surgical instrument is fired and the surgical fasteners are released.

A continuing need exists, however, for improved surgical instruments and methods for performing remote anastomoses during both conventional and minimally invasive procedures which reduce the likelihood of leaks due to tissue slippage.

SUMMARY

The present disclosure relates to a surgical fastener for use with an anastomosis of two tissues. The surgical fastener is generally L-shaped and includes a base leg and an upright leg. The base leg is selectively deformable and includes a traumatic tip for piecing tissue and the upright leg includes a prong which preferably extends atraumatically against the tissue. The surgical fastener also includes a capillary disposed on the base leg which has a reservoir defined therein for retaining a liquid. The capillary (or capillaries) is designed to rupture upon deformation of the surgical fastener to dispense the liquid to the anastomosis site. It is envisioned that many different staple design may be used with one or more capillaries disposed on the deformable portions thereof. Which are designed to rupture upon deformation to expel the liquid disposed therein?

In one embodiment, the liquid in the reservoir includes a bonding agent, a medicinal agent and/or a therapeutic agent. Preferably, the medicinal agents or therapeutic agents include: anti-coagulants, bio-adhesives, coagulants; antibiotics, sterilizing solutions, anti-inflammatory medication, inflammatory medications; immuno-stimulating agents, antiviral agents and/or anti-rejection medications. The bonding agent is preferably made from a material which adheres to tissue upon curing. As can be appreciated from the present disclosure, this staple design enables a bonding agent to be accurately and efficiently delivered to the anastomotic site which may promote better anastomoses between tissues, promote healing, reduce leakage at the tissue-to-tissue site, and reduce infection.

In another embodiment, the reservoir includes a series of chambers which each include a liquid disposed therein selected from the group consisting of: bonding agents, medicinal agents and therapeutic agents.

In yet another embodiment, the surgical fastener includes a base leg of having first and second capillaries which are designed to sequentially rupture upon deformation. It is envisioned that the first capillary may include a medicinal agent and the second capillary may include a bonding agent or other agent. Preferably, the capillaries are radially disposed along the base leg of the surgical fastener.

The present disclosure also relates to a surgical fastener for use with a surgical instrument for performing an anastomosis between two tissues. The surgical instrument includes a selectively enageable loading unit (e.g., a single-use loading unit or "SULU") for supporting an array of surgical fasteners and an actuator (handle) for initiating deformation of the surgical fasteners. Each of the surgical fasteners includes a base leg and an upright leg. The base leg is selectively deformable and includes a tip for piecing tissue. At least one capillary is disposed on the base leg and includes a reservoir defined therein for retaining a liquid such as a bonding agent, medicinal agent and/or therapeutic agent. Each of the capillaries is ruptures upon deformation to dispense the liquid to the anastomosis site.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

An illustrative embodiment of the subject surgical fastener is described herein with reference to the drawings wherein:

FIG. 5 is a perspective view of the SULU with a first vessel inserted the therethrough;

FIG. 6 is perspective of the SULU with an end of the first vessel everted over a distal end of the disposable unit being inserted into an incision in a second vessel;

FIGS. 18A-18C are views showing alternate configurations for the surgical fastener.

DETAILED DESCRIPTION

Figure 1:
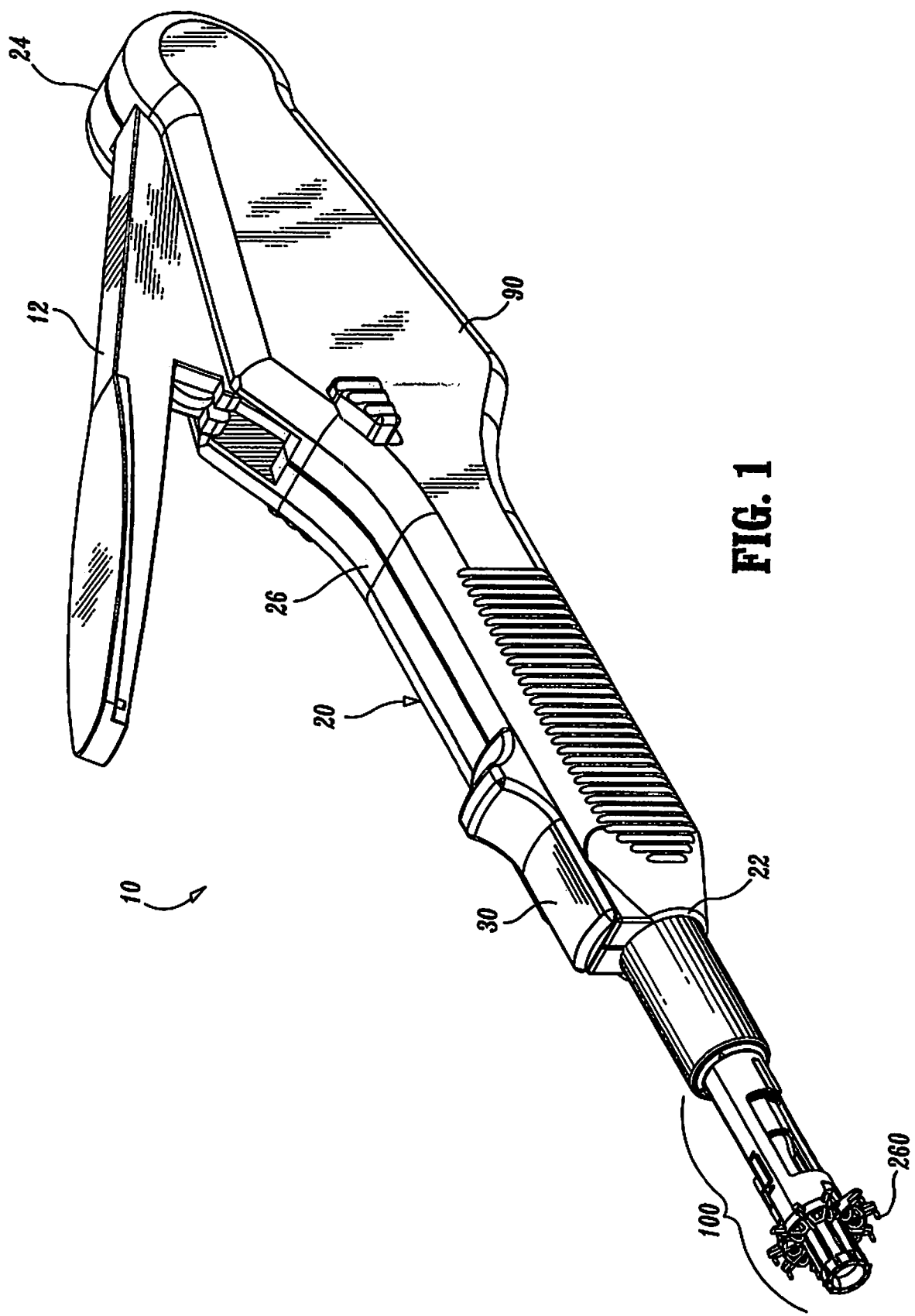
FIG. 1 is a perspective view of a surgical instrument for use with a surgical fastener in accordance with an embodiment of the present disclosure.

Preferred embodiments of the surgical fastener disclosed herein will be described in terms of a surgical instrument used for coronary artery bypass procedures wherein a vascular anastomosis is created by joining a section of a harvested vessel, e.g., the saphenous vein, to bypass an occlusion in a coronary artery, e.g., the left anterior descending artery ("LAD"). Alternatively, the presently disclosed surgical instrument may also be utilized in performing anastomosis of other tubular luminal body structures, e.g., colon resection.

In the drawings and in the description which follows, the term "proximal", as is traditional, will refer to the end of the apparatus which is closer to the user, while the term "distal" will refer to the end which is further from the user.

Figure 8:
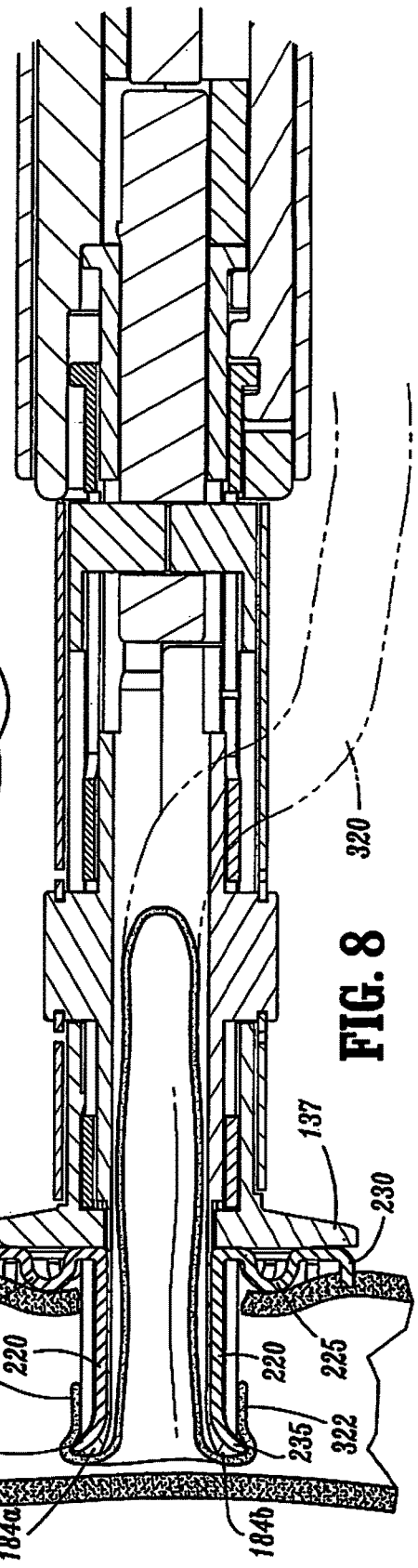
FIG. 8 is a side cross-sectional view of the SULU and the everted first vessel shown inserted within the second vessel in pre-firing position.

Referring now in detail to the drawing figures in which like reference numerals identify similar or identical elements, one embodiment of an instrument for use with a surgical fastener 200 according the to present disclosure is shown by way of example in FIG. 1 and is designated therein—as surgical instrument 10. As explained in more detail below, surgical instrument 10 includes two principal components, namely, an actuator assembly 20 and a disposable loading unit ("DLU") or a single use loading unit ("SULU") 100, which along with their internal working components, mechanically cooperate to deform the surgical fastener 200 to complete an anastomosis between two vessels, e.g., a saphenous vein 320 and an aorta 310 (FIG. 8). Surgical instrument 10 is preferably designed to deform an array of surgical fasteners 200.

Actuator assembly 20 includes a proximal end 24, a distal end 22 and a housing 26 defined therebetween for storing the internal working components of the actuator assembly 20. Preferably, a plate 90 covers the internal components of the actuator assembly 20 when assembled. Actuator assembly 20 also includes a handle 12 which initiates firing of the surgical instrument 10 and a spring-loaded thumb tab 30 for loading the SULU 100 onto the actuator assembly 20 both of which will be explained in greater detail below. Preferably, handle 12 is provided with an ergonomic surface which is contoured and configured to be comfortably gripped by the hand of the user during operation of the instrument.

For the purposes herein, only the general operating features of the surgical instrument 10 are described. However, the internal-working components of surgical instrument 10 are described in detail in commonly-owned U.S. application Ser. No. 10/399,558, filed on Apr. 15, 2003 entitled "ANASTOMOSIS INSTRUMENT AND METHOD FOR PERFORMING SAME" the contents of which are hereby incorporated by reference herein in its entirety.

Figure 4A:
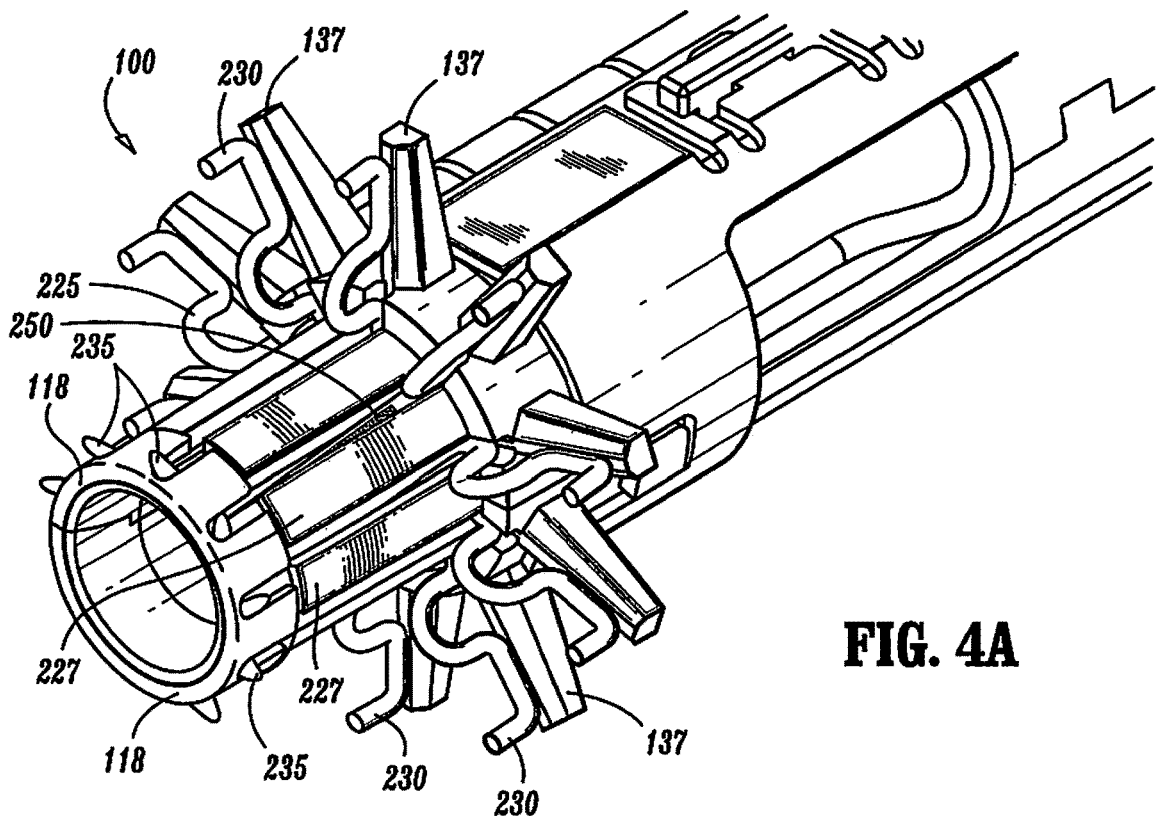
FIG. 4A is an enlarged, partial perspective view of a single use loading unit (SULU) which is designed to support an array of surgical fasteners and which is designed for operative engagement with a working end of the surgical anastomosis instrument.
Figure 4B:
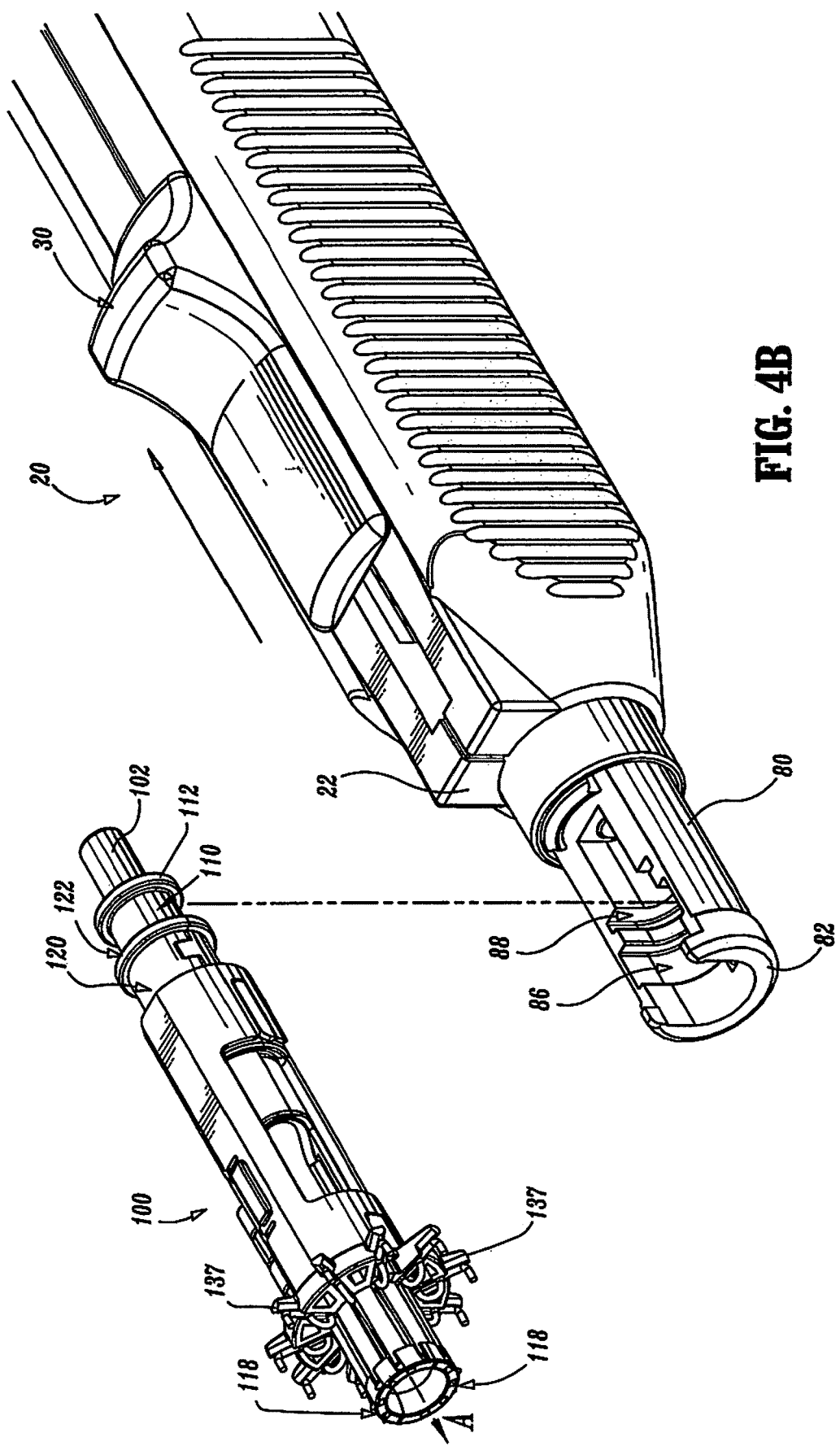
FIG. 4B is an enlarged perspective view of the SULU being loaded onto an actuating assembly prior to firing.
Figure 11:
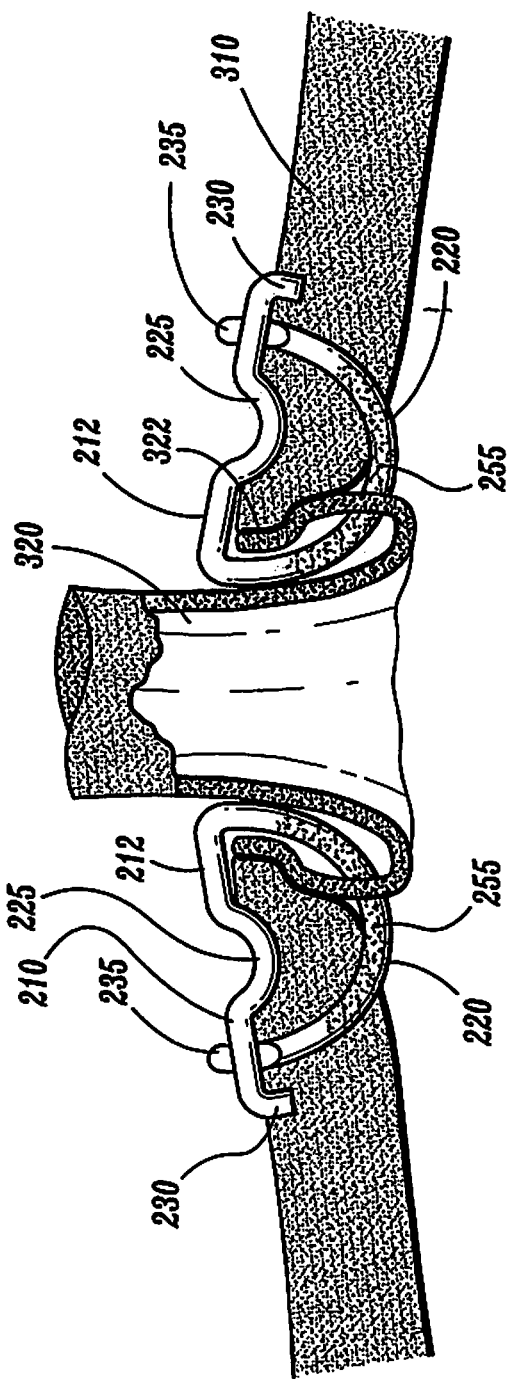
FIG. 11 is cross section of the two luminal vessels showing the bonding agent retaining the surgical fastener in position after firing.

As best shown in FIGS. 4A and 4B, the SULU 100 includes a first retracting sleeve 110 and second retracting sleeve 120 which cooperate to deform fasteners 200 and securely fasten the saphenous vein 320 to the aorta 310 in fluid communication (see FIG. 11). More particularly, retracting sleeve 110 includes a circular lip 112 located at its proximal end and a semi-circular anvil 118 located at the opposite end. Movement of the first retracting sleeve 110 deforms the surgical fasteners 200. Movement of the second retracting 120 sleeve releases the surgical fasteners 200. The operative details associated with the inter-cooperative relationship of the SULU 100 and the actuator assembly 20 are described in more detail with respect to commonly-owned U.S. patent Ser. No. 10/160,460 the entire contents of which are hereby incorporated by reference herein. For the purposes herein, only a limited discussion of the working features of the SULU 100 and the actuator assembly 20 is warranted.

As best seen in FIG. 4B, movement of tab 30 will expose carriages 86 and 88 disposed within a first retractor 80 in the distal end of the actuating assembly. The carriages 88 and 86 are designed to receive the first and second retracting sleeves 110 and 120, respectively. More particularly, carriage 86 is generally circular in shape and is designed to receive an outer lip 122 of second retracting sleeve 120. Carriage 88 is likewise circular in shape and receives outer lip 112 of the first retracting sleeve 110.

The SULU 100 is then loaded within actuator assembly 20 by placing lip 112 within carriage 88 and lip 122 within carriage 86. Lip 122 is positioned near the distal end of carriage 86 which allows lip 122 and, hence, second retracting sleeve 120, to move independently from the first retracting sleeve to release the surgical fasteners after deformation. Once the SULU is positioned within carriages 86 and 88, thumb tab 30 is released to lock the SULU 100 within the actuator assembly 20.

Figure 10A:
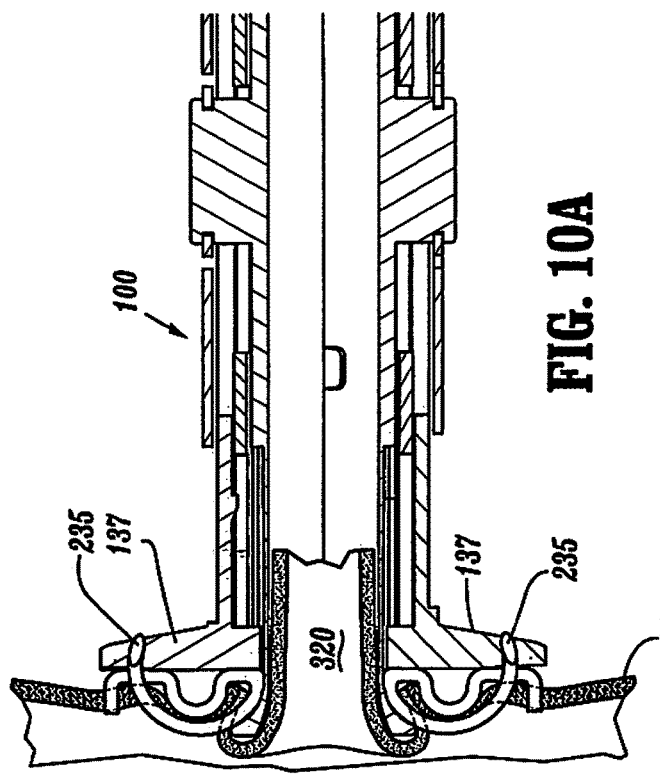
FIG. 10A is an enlarged, perspective view of the SULU and the surgical fastener shown after firing.

As mentioned above, upon actuation of actuator assembly 20, the first retractor 80 retracts the first retracting sleeve 110 which, in turn, causes surgical fasteners 200 to deform. More particularly, proximal movement of the first retractor 80 causes both the first retracting sleeve 110 and the second retracting sleeve 120 to move proximally relative to a biasing post 102 on the end of the SULU 100. As a result, the anvil 118 deforms the distal ends 235 of surgical fasteners 200 upwardly and proximally towards a series of corresponding support braces 137 located on the SULU. The arc-like distal ends of the anvil 118 cause surgical fasteners 260 to deform upwardly and proximally upon retraction of the first retracting sleeve 110. FIG. 10A illustrates the resulting deformation of the surgical fastener 200 through the two luminal structures 320 and 310.

Figure 10B:
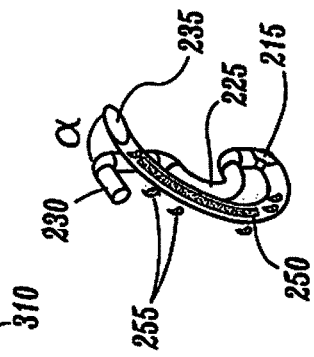
FIG. 10B is a greatly enlarged, perspective view of the surgical fastener shown in a "stapled" configuration.

Preferably, the opposite ends 235 and 230 of the surgical fasteners 200 are deformed at an angle a relative to one another as best shown in FIG. 10B. This allows end 235 to deform proximal to braces 137. Preferably, braces 137 have a tapered cross section to further deform end 235 of surgical fastener 200 radially from end 230 during deformation.

Figure 2:
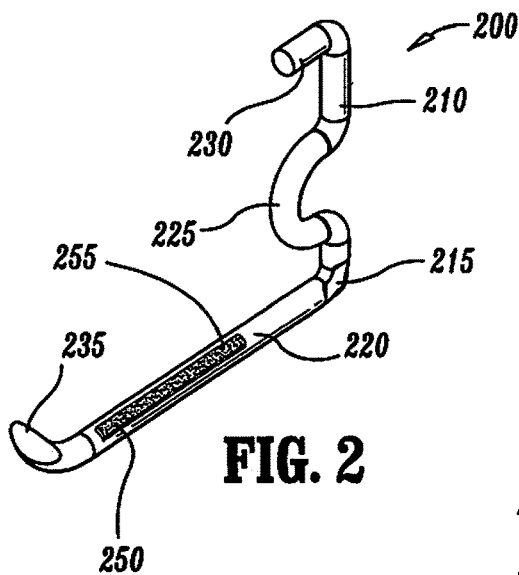
FIG. 2 is an enlarged, perspective view of the surgical fastener according to the present disclosure showing a set of bonding agent capillaries disposed on a base leg thereof.
Figure 3:
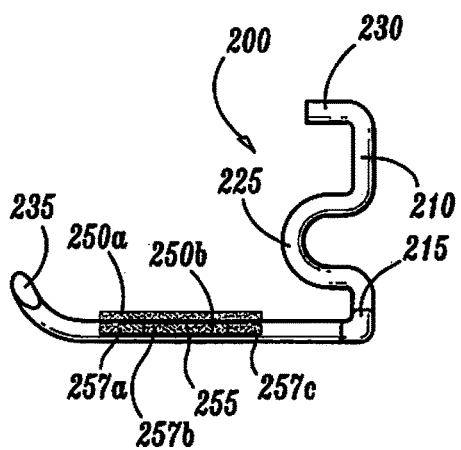
FIG. 3 is an enlarged, side view of the surgical fastener of FIG. 2.

As best seen in FIGS. 2 and 3, surgical fastener 200 is generally L-shaped and includes a base leg 220 and an upwardly extending support leg 210. Preferably, base leg 220 includes a distal end 235 which is sufficiently shaped to penetrate the saphenous vein 320 and aorta 310 upon deformation of the surgical fastener 200. The upwardly extending support leg 210 is attached to base leg 220 at a pivot point 215 and includes an inwardly extending prong 230 disposed at its free end designed to penetrate the aorta 310 and secure surgical fastener 200 in position after anastomosis. It is envisioned that pivot point 215 may also be dimensioned to include a relief or coined section (not shown) which will facilitate deformation of the surgical fastener 200.

A convexity 225 projects inwardly between the base leg 220 and the support leg 210 and is preferably sufficiently dimensioned to cooperate with the base leg 220 to retain the saphenous vein 320 against aorta 310 in fluid communication after anastomosis as will be explained in greater detail below. It is envisioned that the surgical fastener 260 can be arranged on the SULU in different patterns/arrays depending upon a particular purpose.

Surgical fastener also includes a capillary 250a which extends along base leg 220. Capillary 250a includes an internal reservoir design to retain a bonding agent 255 therein. The term "bonding agent" is defined herein to include fluids and gels (e.g., hydrogels and gelatins), which having the ability to bond two tissues together under compression. As can be appreciated different bonding agents with different bonding characteristics, e.g., strength, duration (as it relates to the biodegradability of the bonding agent), tackiness, curing attributes, etc. may be employed depending upon a particular purpose.

It is envisioned that the capillary 250a may contain one or more reservoirs 257a-257c which contain one or more bonding agents 255 (or other medicinal agents) depending upon a particular purpose (e.g., designed to activate upon mixing). In some instances it may be desirable to utilize more than one capillary, e.g., 250b. Moreover, one of the capillaries 250a (or one of the reservoirs 257a-257c in a single capillary system) may contain a bonding agent 255 and another, e.g., 250b may contain additional bonding agents or other medicinal agents or therapeutic agents such as: anti-coagulants, bio-adhesives (e.g., polymer-based, co-polymer based, organic compounds, barnacle-based, plant-based, Progesterone-based, etc.), coagulants; antibiotics, sterilizing solutions, anti-inflammatory medication, inflammatory medications (which may help secure seal as explained in more detail below); immuno-stimulating agents, antiviral agents and/or anti-rejection medications.

The capillary (or capillaries) are designed to rupture upon deformation of the surgical fastener 200 thereby releasing the bonding agent(s) atop and along each surgical fastener. Preferably, the capillary ruptures at multiple locations along the length thereof to more evenly disperse the bonding agent along the surgical fastener 200. It is also envisioned that the capillary can be designed to rupture sequentially at multiple positions along the length thereof which would allow sequential mixing of bonding agents and/or other medicinal agents.

As best illustrated in FIGS. 10A-11, by design, the capillary 250 is designed to rupture simultaneously upon deformation of the surgical fastener 200. As can be appreciated, this enables the bonding agent to dispense along the base leg 220 of the surgical fastener between the two tissues. Preferably, the bonding agent 255 quickly cures to seal both the pierced areas of the tissues and secure the surgical fastener 200 to the tissues to prevent slippage. As mentioned above, the bonding agent 255 may be a composition of medicinal agents and adhesives which promote healing and/or reduce the chances of infection around the anastomotic site. In addition, it is envisioned that a bonding agent 255 may be employed which slightly expands upon curing to facilitate sealing of the pierced tissues after firing.

As mentioned above and as best seen in FIGS. 10A and 11, the convexity 225 of the surgical fastener projects inwardly between the base leg 220 and the support leg 210 to retain the saphenous vein 320 against aorta 310 in fluid communication after anastomosis. More particularly, after deformation of the surgical fastener 200, the convexity 225 is designed to assert a consistent pressure against the aorta 310 to squeeze the two tissues 310 and 320 into tight abutment with one another.

It is envisioned that the surgical fastener 200 can be other or more conventional shapes to enhance anastomosis between the two tissues 310 and 320.

Figure 13:
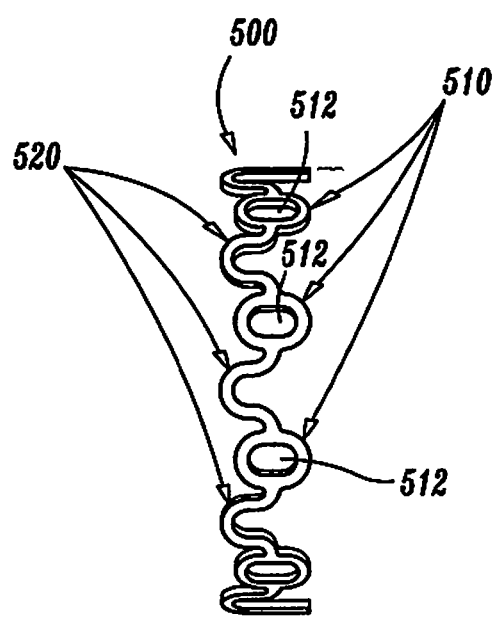
FIG. 13 shows a retaining ring for use with the surgical fastener.

A retaining ring or strap may also be utilized to maintain a consistent anastomosis between the two luminal vessels 310 and 320 after the SULU 100 is fired and the surgical fasteners 200 are released (See FIG. 13). More particularly, retaining ring includes a series of alternating loops and arcuate portions which are formed radially about the ring. Each loop defines an aperture therein which is dimensioned to receive the distal end 2235 of a surgical fastener 200. Several examples of retain rings and straps are disclosed in U.S. patent application Ser. No. 10/160,460 the entire contents of which are hereby incorporated by reference herein.

Turning now in detail to the operation of the surgical instrument 10 and in particular, the operation of the SULU 100 as detailed in FIGS. 5-10B, once the saphenous vein 320 has been harvested, the user inserts the free end 322 into opening 133 of the SULU 100 and pulls (via a surgical hook or graspers) the free end 322 towards the distal end of the SULU 100. The user then everts the saphenous vein 320 over the anvil 118 of the SULU 100 such that the free end 322 of the saphenous vein 320 is retained by end 235 of the surgical fasteners 200. Everting of the saphenous vein 320 may be achieved by any suitable known instruments and/or techniques such as by using graspers.

Figure 7:
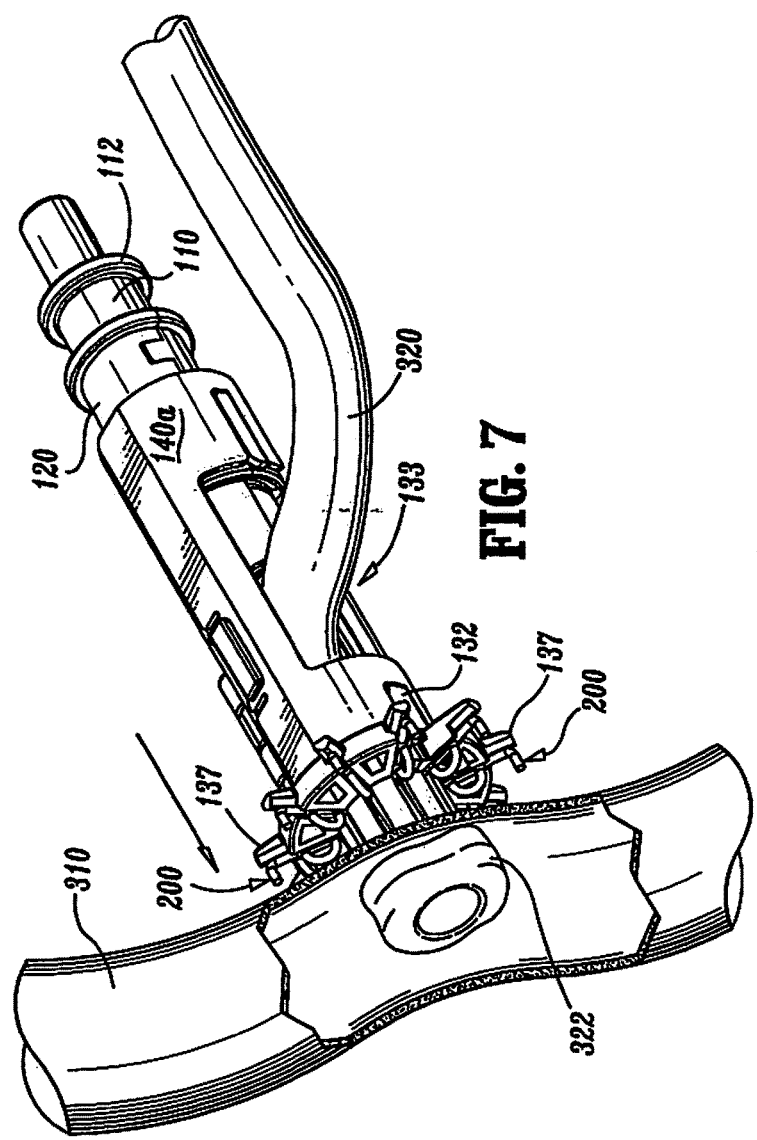
FIG. 7 is an internal, perspective view of the second vessel with the SULU and the everted first vessel shown inserted therein.

The remaining portion of the saphenous vein 320 is preferably positioned away from the instrument 10 to facilitate insertion of the saphenous vein 320 into the aorta 310 as shown in FIGS. 6 and 7. The user then inserts the end of the SULU 100 into an incision 312 in the aorta 310 such that the distal end 235 of each of the plurality of fasteners 200 and the everted end portions 322 of the saphenous vein 320 are sufficiently inserted into and through incision 312 (FIGS. 7 and 8). As seen best in the enlarged view of FIG. 8, the support leg 210, convexity 225 and prong 230 of each surgical fastener 200 remains outside incision 312. The instrument is now preset for firing.

Figure 9:
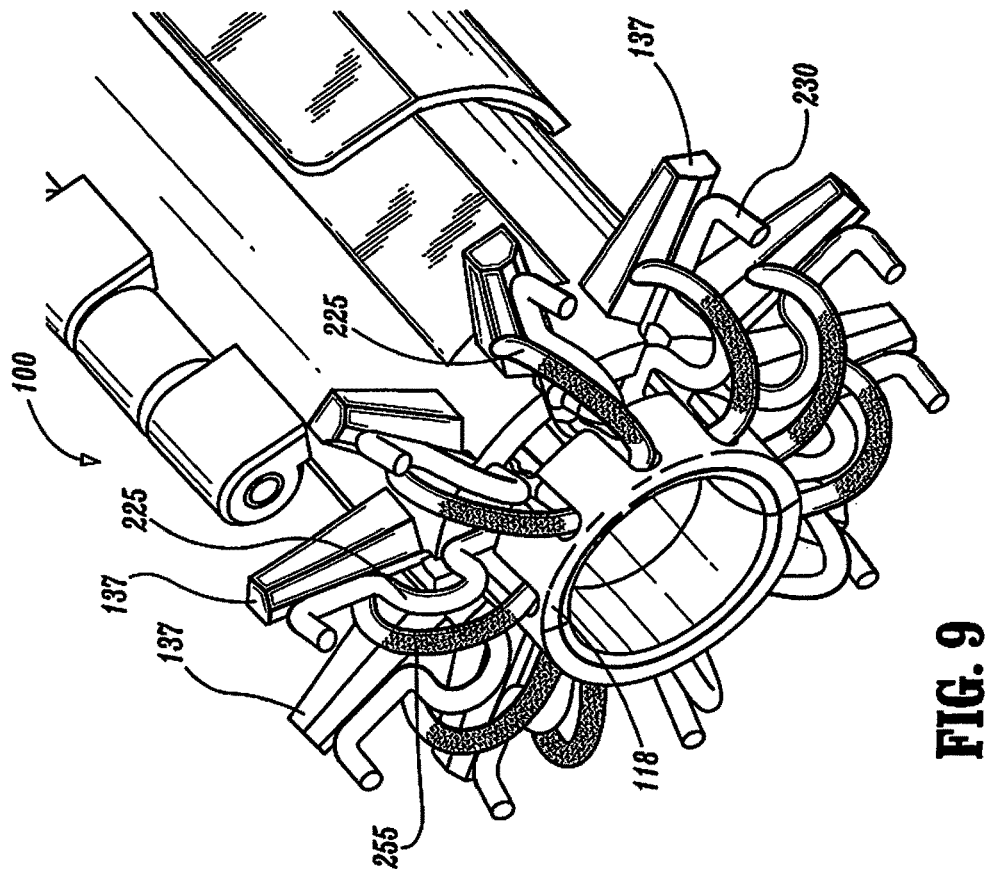
FIG. 9 is an enlarged, perspective view of the SULU and the surgical fastener shown after firing.
Figure 12:
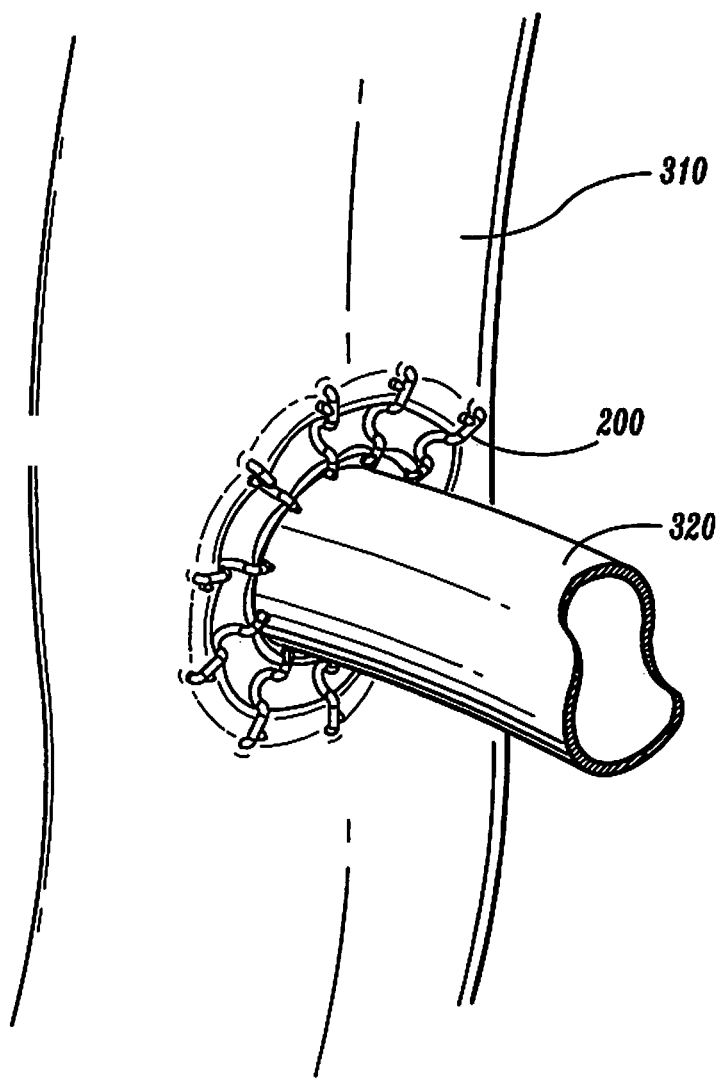
FIG. 12 is a view showing a completed anastomosis.

When the handle 12 is depressed by the user, it ultimately moves the retractor 80 proximally to retract the first retracting sleeve 110 which, in turn, causes surgical fasteners 200 to deform as shown in FIGS. 9-10B. More particularly, proximal movement of the first retractor 80 causes both the first retracting sleeve 110 and the second retracting sleeve 120 to move proximally relative to biasing post 102. As a result, anvil 118 deforms the distal ends 235 of surgical fasteners 200 upwardly and proximally towards brace 137. At the same time, the aorta 310 is forced slightly proximally and extending prongs 230 penetrate to hold the aorta 310 in position as best seen in FIG. 10A. As mentioned above, the opposite ends 235 and 230 of the surgical fasteners 200 are deformed at an angle a relative to one another which allows end 235 to deform proximally past braces 137. FIG. 12 shows a completed anastomosis.

In use, surgical instrument 10 facilitates the performance of a vascular anastomosis and either eliminates and/or minimizes the need for manual suturing of the vessels. Although the uses described herein will be addressed in terms of vascular anastomosis performed on a beating heart, the presently disclosed surgical instrument 10 and surgical fastener 200 may also be used in performing anastomoses of other tubular or luminal body structures without departing from the scope herein. For example, surgical instrument 10 may be used in conventional open CABG procedures using a median sternotomy or other large incision without stopping the heart. Alternatively, the thoracic "window" procedure may be used to achieve access to the heart. The "window" approach involves a smaller incision and less displacement of the ribs, and therefore is less traumatic to the patient. For this approach, conventional surgical techniques are used to determine the location of the incision to access the chest cavity.

To gain access to the heart, after an incision is made, a surgical retractor assembly may be used to separate the ribs at the site of the incision. Specifically, the retractor assembly is mounted on a base and used to retract ribs until a sufficiently large opening in the chest cavity is defined to provide direct access to the heart. For example, the sternum and the fourth and fifth ribs can be split apart to create a window. Other configurations of spreading the ribs and/or selectively cutting individual ribs away from the sternum may also be utilized for a particular procedure.

Once the desired access to the heart is achieved, the graft vessel, e.g., the saphenous vein 320 is dissected and harvested from the leg, and a free end of the vessel is exposed. The occluded coronary artery, e.g., the LAD 310, is then prepared for receiving the saphenous vein 320 graft. The heart is positioned in the desired orientation either by traction sutures passing through the pericardium or by manipulation with heart manipulation instruments which are held by the surgical personnel or clamped in a fixed orientation to a base such as the retractor assembly base. Blood flow through the aorta 310 can be restricted by cardiopulmonary bypass and pericardial cooling. Alternatively, a dampening instrument may be applied directly on the aorta 310 to restrict blood flow and reduce movement of the heart near the aorta 310.

Continual movement of the handle 12 after deformation of the surgical fasteners 200, moves the second retracting sleeve 120 within carriage 86 relative to the first retracting sleeve 110. Proximal movement of the second retracting sleeve 120 releases the surgical fasteners 200 after deformation. A more detailed explanation relating to the release of the surgical fasteners is disclosed in U.S. patent application Ser. No. 10/160,460 the entire contents of which are hereby incorporated by reference herein.

Figure 15:
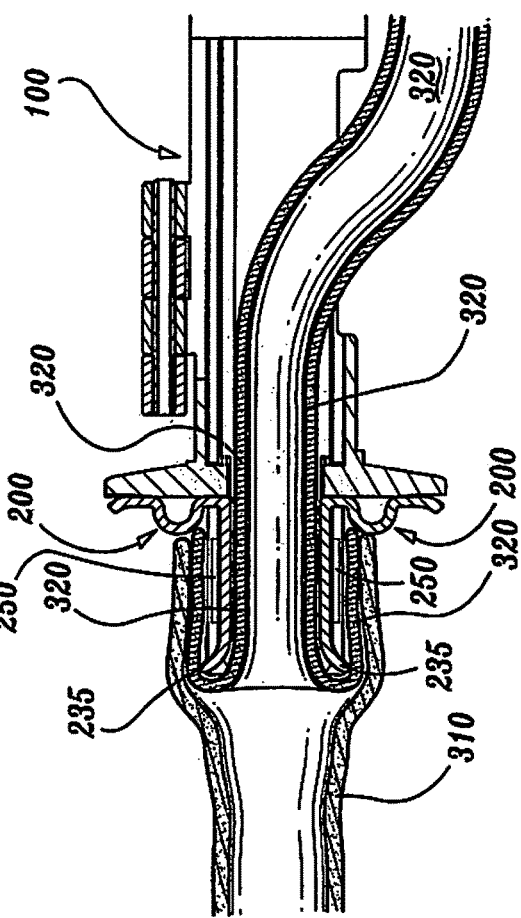
FIGS. 14-17 show a series of surgical fasteners being used during an end-to-end anastomosis.
Figure 14:
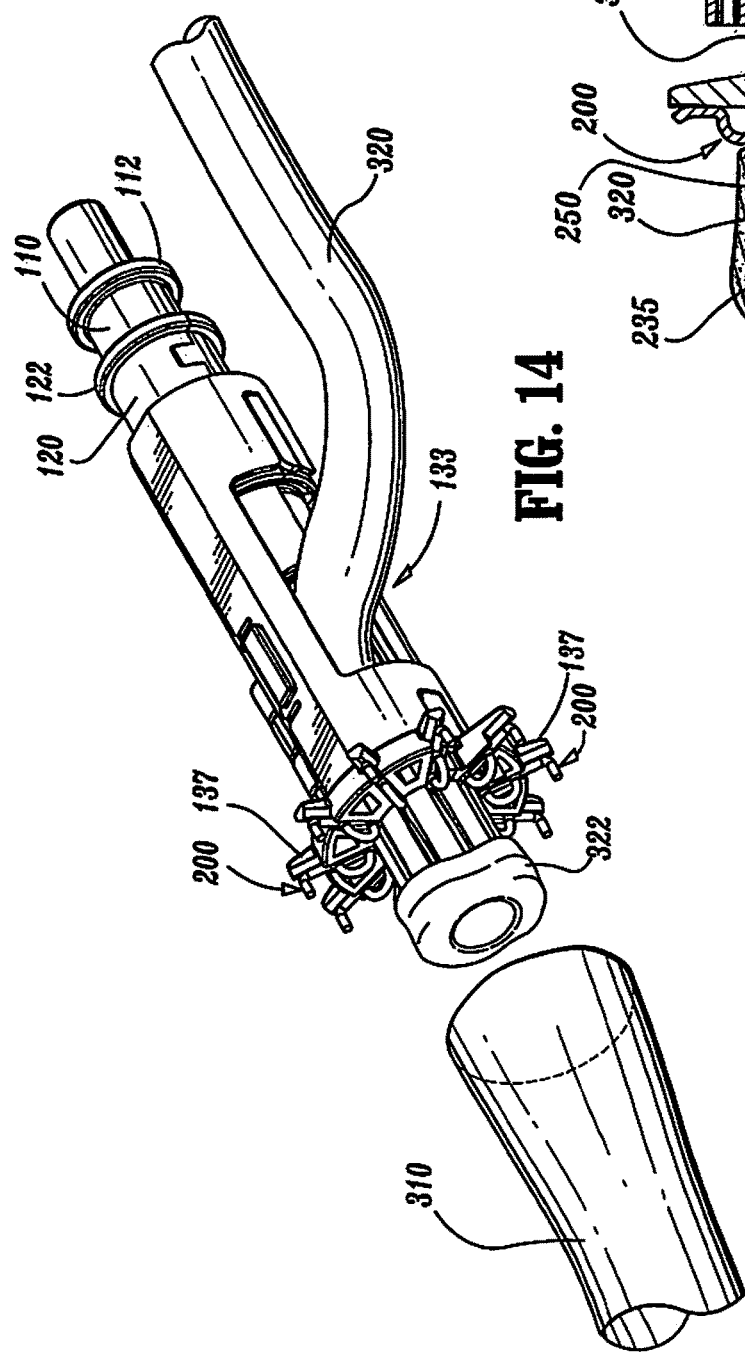

FIGS. 14-17 show the presently disclosed staple for use with an end-to-end anastomosis. More particularly, the user inserts a free end 322 of the first luminal structure, e.g., intestine, into opening 133 of the SULU and pulls via a surgical hook or graspers the free end 322 towards the distal end of the SULU 100. The user then everts the first luminal structure 320 over the anvils 118 of the SULU 100 such that the free end 322 is retained by end 235 of the surgical fasteners 200 (see FIG. 14). Everting of the first luminal structure 320 may be achieved by any suitable known instruments and/or techniques such as by using graspers. The first luminal structure 320 is preferably everted over the full length of the base leg 220 such that the first luminal structure 320 resides in close proximity to convexity 225 as best seen in FIG. 15.

The first luminal structure 320 may then secured to the distal end of the SULU 100 by a suture or other convention means or by virtue of an additional securing mechanism (not shown) disposed on the SULU 100. The user then inserts the end of the SULU 100 and the first luminal structure 320 into the second luminal structure 310 such that the distal end 255 of each of the plurality of fasteners 200 and the everted end portions 322 of the first luminal structure 320 are sufficiently inserted into end 312 (FIG. 15). The support leg 210, convexity 225 and prong 230 of each surgical fastener 200 remains outside opening 312. The instrument is now preset for firing.

Figure 16:
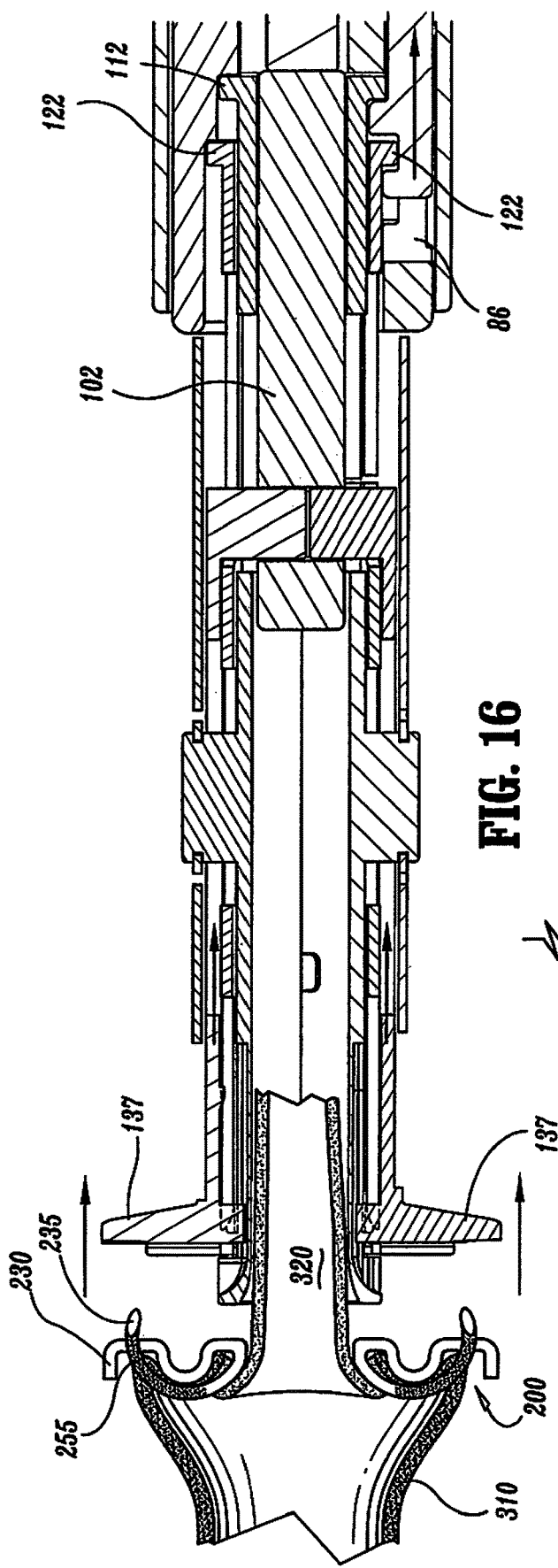
Figure 17:
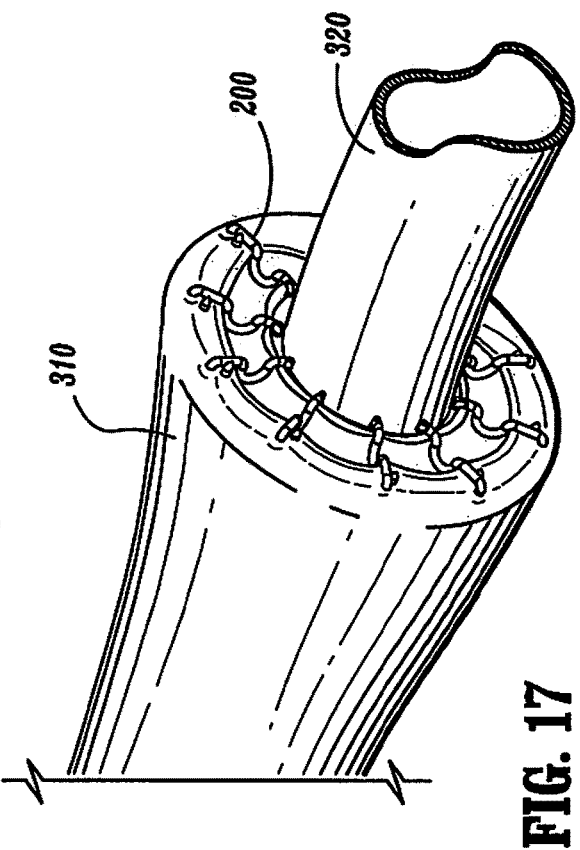

Much in a similar manner as described above, when the handle 12 is actuated by the user, it ultimately moves the retractor 80 proximally to retract the first retracting sleeve 110 which, in turn, causes surgical fasteners 200 to deform as shown in FIG. 16. More particularly, proximal movement of the first retractor 80 causes both the first retracting sleeve 110 and the second retracting sleeve 120 to move proximally relative to biasing post 102. As a result, anvil 118 deforms the distal ends 235 of surgical fasteners 200 upwardly and proximally towards brace 137. At the same time, the aorta 310 is forced slightly proximally and extending prongs 230 penetrate to hold the aorta 310 in position as best seen in FIG. 16. As mentioned above, the opposite ends 235 and 230 of the surgical fasteners 200 are deformed at an angle a relative to one another which allows end 235 to deform proximally past braces 137. FIG. 17 shows a completed anastomosis.

As mentioned above, the first retractor 80 retracts the first retracting sleeve 110 (FIG. 21) which, in turn, causes surgical fasteners 260 to deform as shown in FIGS. 21B and 21D. More particularly and as best shown in FIG. 21B, proximal movement of the first retractor 80 causes both the first retracting sleeve 110 and the second retracting sleeve 120 to move proximally relative to biasing post 102 until biasing post 102 abuts the end 69 of elongated stop 65. As a result, anvils 118a and 118b deform the distal ends 269 of surgical fasteners 260 upwardly and proximally towards braces 137a and 137b, respectively, i.e., arc-like distal ends 184a and 184b cause surgical fasteners 260 to deform upwardly and proximally upon retraction of the first retracting sleeve 110. At the same time, the second luminal structure 310 is forced slightly proximally and extending prongs 267 penetrate to hold the second luminal structure 310 in position as best seen in FIG. 22A. FIG. 26 illustrates the resulting deformation of clip 260 through the two luminal structures 320 and 310.

It is anticipated that the radially offset orientation of the opposite ends 186a, 186b and 184a, 184b of the support channels 119a and 119b, respectively will cause the opposite ends 267 and 269 of the surgical fasteners 260 to deform at an angle a relative to one another as best shown in FIG. 21D. This allows end 269 to deform proximal to braces 137a and 137b. Preferably, braces 137a and 137b have a tapered cross section to deform end 269 of surgical fastener 260 radially from end 267 during deformation.

It is anticipated that the presently disclosed surgical fasteners 260 can also include an end 269 which is blunt and which does not penetrate the luminal structures 320 or 310 upon deformation. As can be appreciated, this offers the user the option of performing a less traumatic anastomosis.

FIGS. 18A-18D show configurations for various surgical fasteners which may include one or more capillaries which when deformed expel a bonding agent therefrom.

From the foregoing and with reference to the various figure drawings, those skilled in the art will appreciate that certain modifications can also be made to the present disclosure without departing from the scope of the same. For example, it may be preferable to position the capillaries 250 at different locations on the surgical fasteners 200 depending upon a particular purpose or to achieve a particular result. Moreover, at least one of the ends of one or more surgical fasteners may include a plurality of tips for piercing tissue. In addition, one of the end of the surgical fastener, e.g., 235, may be traumatic, while the other end may be atraumatic (i.e., does not pierce tissue). Alternatively, both ends of the surgical fastener 235 may be atraumatic.

It is also envisioned that the surgical fastener 200 may include two or more capillaries 250*a*, 250*b* which are radially disposed along the length of the base member 220.

It will be understood that various modifications may be made to the embodiments shown herein. For example, the instrument may be sized to perform an anastomosis for other vessels and luminal tissue, e.g., intestine, bowel, colon, etc. Therefore, the above description should not be construed as limiting, but merely as exemplifications of preferred embodiments. Those skilled in the art will envision other modifications within the scope and spirit of the claims appended hereto.

What is claimed is:

1. A surgical instrument comprising:
   an actuator assembly;
   a loading unit coupled to the actuator assembly, the loading unit including a plurality of surgical fasteners, the actuator assembly configured to actuate the loading unit to fire the plurality of surgical fasteners from the loading unit, each surgical fastener of the plurality of surgical fasteners including:
   a first leg;
   a second leg; and
   a pivot point connecting the first and second legs,
   at least one capillary disposed on one of the first or second legs, the at least one capillary rupturable upon deformation of the one of the first or second legs to dispense a liquid disposed within the capillary.

2. The surgical instrument according to claim 1, wherein the at least one capillary is disposed in a reservoir defined in one of the first or second legs.

3. The surgical instrument according to claim 2, wherein the liquid disposed within the at least one capillary includes at least one of a bonding agent, medicinal agent, or therapeutic agent.

4. The surgical instrument according to claim 2, wherein the reservoir includes a series of chambers, each of the chambers including a liquid disposed therein selected from the group consisting of bonding agents, medicinal agents, and therapeutic agents.

5. The surgical instrument according to claim 1, wherein the liquid is selected from the group consisting of an anti-coagulant, a bio-adhesive, a coagulant, an antibiotic, a sterilizing solution, an anti-inflammatory medication, an inflammatory medications, an immuno-stimulating agent, an antiviral agent, and an anti-rejection medication.

6. The surgical instrument according to claim 1, wherein the liquid is a bonding agent designed to adhere to tissue upon curing.

7. The surgical instrument according to claim 1, wherein the first leg of the surgical fastener includes capillary plurality of capillaries, the plurality of capillaries configured to rupture upon deformation of the first leg.

8. The surgical instrument according to claim 7, wherein the each capillary of the plurality of capillaries is configured to rupture sequentially.

9. The surgical instrument according to claim 7, wherein at least one of the plurality of capillaries includes a medicinal agent and another of the plurality of capillaries includes a bonding agent.

10. The surgical instrument according to claim 7, wherein at least one of the plurality of capillaries includes a bonding agent activatable in response to exposure to a curing agent and another of the plurality of capillaries includes the curing agent.

11. The surgical instrument according to claim 1, further comprising a plurality of capillaries, each of the plurality of capillaries disposed on one of the first or second legs, at least two of the plurality of capillaries radially disposed relative to one another about one of the first or second legs of the surgical fastener.

12. The surgical instrument according to claim 1, wherein the at least one capillary is configured to rupture at multiple locations along the length thereof.

13. The surgical instrument according to claim 1, wherein the first leg includes a traumatic tip for piercing tissue.

14. The surgical instrument according to claim 1, wherein loading unit is a single use loading unit.

15. The surgical instrument according to claim 1, wherein the loading unit includes an anvil, the anvil configured to deform the surgical fastener in response to actuation of the actuation assembly.

16. The surgical instrument according to claim 1, wherein the loading unit is releasably coupled to the actuation assembly.

17. A surgical instrument comprising:
   an actuator assembly;
   a loading unit coupled to the actuator assembly, the loading unit including a plurality of surgical fasteners, the actuator assembly configured to actuate the loading unit to fire the plurality of surgical fasteners from the loading unit, each surgical fastener of the plurality of surgical fasteners having:
   a base leg and an upright leg, the base leg selectively deformable and including a traumatic tip for piercing tissue; and
   at least one capillary disposed on the base leg having a reservoir defined therein for retaining a liquid, each of the at least one capillary rupturable upon deformation of the surgical fastener to dispense the liquid as the surgical fastener is ruptured.

18. The surgical instrument according to claim 17, wherein the liquid in the reservoir includes at least one of a bonding agent, a medicinal agent, or a therapeutic agent.

19. The surgical instrument according to claim 17, wherein the liquid is a bonding agent configured to adhere to tissue upon curing.

20. The surgical instrument according to claim 17, wherein the base leg of the surgical fastener includes at least two capillaries, the at least two capillaries configured to sequentially rupture upon deformation of the base leg.

* * * * *